(12) United States Patent
Fu (10) Patent No.: US 7,906,273 B2
(45) Date of Patent: Mar. 15, 2011

(54) METHOD OF MANUFACTURING HOLLOW MICRO-NEEDLE STRUCTURES

(75) Inventor: Chien-Chung Fu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 971 days.

(21) Appl. No.: 11/798,884

(22) Filed: May 17, 2007

(65) Prior Publication Data

US 2007/0275521 A1 Nov. 29, 2007

(30) Foreign Application Priority Data

May 26, 2006 (TW) .................................. 95118709 A (51) Int. Cl.
*G03F 7/00* (2006.01)
(52) U.S. Cl. ......................................................... 430/320
(58) Field of Classification Search .......................... None
See application file for complete search history.

(56) References Cited

U.S. PATENT DOCUMENTS

| | | | |
|---|---|---|---|
| 6,406,638 | B1 | 6/2002 | Stoeber et al. |
| 2003/0009113 | A1 | 1/2003 | Olson |
| 2004/0072105 | A1* | 4/2004 | Yeshurun et al. ............. 430/313 |
| 2005/0011858 | A1 | 1/2005 | Kuo et al. |
| 2006/0055090 | A1* | 3/2006 | Lee et al. ....................... 264/494 |
| 2006/0084942 | A1* | 4/2006 | Kim et al. ................... 604/890.1 |
| 2006/0275711 | A1* | 12/2006 | Fu et al. ........................ 430/320 |

FOREIGN PATENT DOCUMENTS

| | | |
|---|---|---|
| JP | 63149032 | 6/1988 |
| TW | 568790 | 1/2004 |
| TW | 225465 | 12/2004 |
| WO | WO-0133614 | 5/2001 |

OTHER PUBLICATIONS

Fu et al. "Different methods for the fabrication of UV-LIGA molds using SU-8 with tapered de-molding angles" Microsyst Technol (2006) DOI 10.1007/00542-006-0197-9.
Fu et al. Internet Article "Different methods for the fabrication of UV-LIGA molds using SU-8 with tapered de modling angles" Published online May 20, 2006, Microsystem Technologies.
Wang et al., "A Novel Fabrication Approach for Microneedles Using Silicon Micromaching Technology", Nano/Micro Engineered and Molecular Systems, 2006, NEMS '06, 1$^{st}$ IEEE International Conference, pp. 545-549, Jan. 2006.

* cited by examiner

*Primary Examiner* — John A. McPherson
(74) *Attorney, Agent, or Firm* — Muncy, Geissler, Olds & Lowe, PLLC (57) ABSTRACT

A method of manufacturing a hollow micro-needle structure includes the steps of: disposing a first mask layer and a second mask layer respectively aside a first substrate and aside a rear surface of the first substrate, wherein the first substrate is transparent to predetermined light; forming a photoresist layer on the front surface of the first substrate and the first mask layer; providing the predetermined light to illuminate the first substrate in a direction from the rear surface to the front surface so as to expose the photoresist layer to form an exposed portion and an unexposed portion; and removing the unexposed portion to form the micro-needle structure, which is formed by the exposed portion. The micro-needle structure has an inclined sidewall and a through hole surrounded by the inclined sidewall.

16 Claims, 10 Drawing Sheets

METHOD OF MANUFACTURING HOLLOW MICRO-NEEDLE STRUCTURES

BACKGROUND OF THE INVENTION

1. Field of Invention

The invention relates to a method of manufacturing a hollow micro-needle structure, and more particularly to a method of manufacturing a hollow micro-needle structure using a photoresist layer in conjunction with two mask layers.

2. Related Art

At present, a hollow micro-needle array has been adopted to get a blood sample or get a minor fluid sample in the medical technology, may be applied to an injection or a drug delivery patch in the biotechnological applications, or may be used as micro electrodes in the opto-electronic industry. The hollow micro-needle array may be manufactured using various materials, such as a semiconductor material, a polymeric material or a metal material. When the hollow micro-needle array is manufactured by the semiconductor material, the hollow micro-needle array has to be frequently formed on a silicon wafer. The conventional process of manufacturing the hollow micro-needle array by the semiconductor material needs a lot of dry-etching steps, a lot of wet-etching steps and a lot of film depositing steps. Thus, the manufacturing procedures are complicated and time consuming, and the yield is low and the manufacturing cost is high.

The hollow micro-needle manufactured by the conventional manufacturing processes usually has a ball-shaped end having the poor jabbing function. Furthermore, the root end of the air passage in the micro-needle is usually greater than the distal end, thereby limiting the fluid flowing through the micro-needle. In order to keep the size of the inner air passage constant and maintain the intensity of the micro-needle, the density of the micro-needles in the micro-needle array cannot be easily increased. Thus, the fluid sample amount obtained through the micro-needle array and the delivered fluid are often insufficient. The smaller inner air passage also increases the flowing resistance of the fluid. Thus, a larger driving force has to be provided at the root end of the micro-needle, and this also increases the cost of the apparatus using the micro-needle array.

U.S. Patent Publication No. 2005/0011858 provides a micro-needle array and a method for fabricating the hollow micro-needle array, wherein a mold for a tip end portion of the micro-needle is formed according to the anisotropic property of wet-etching, and then the inner air passage of the micro-needle is defined using the patterned photoresist. Thereafter, a metal layer is deposited on the patterned photoresist. Finally, a de-molding procedure and a dry-etching procedure are performed to form the micro-needle. In this patent, the number of manufacturing steps and the number of kinds of manufacturing processes are also very great, which is not advantageous to the decrease of the manufacturing cost. In addition, no hole can be formed on the sidewall of the micro-needle using the technology of the '858 patent.

U.S. Patent Publication No. 2003/0009113 provides micro-needles and methods of manufacture and use thereof. The micro-needles are formed by way of plastic injection molding. Thus, the mold has to be very precise and the de-molding angle has to be designed very precisely. The micro-needles are only suitable for the mass production. In addition, no hole can be formed on the sidewall of the micro-needle using the technology of the '113 patent.

Thus, it is an important subject of the invention to provide a method of manufacturing a micro-needle structure in a simple manner.

SUMMARY OF THE INVENTION

It is therefore an object of the invention to provide a method of manufacturing a hollow micro-needle structure, which is suitable for the applications of the biomedical industry and the opto-electronic industry, has a low cost and may be easily formed into a hollow micro-needle array structure.

The invention achieves the above-identified object by providing a method of manufacturing a hollow micro-needle structure. The method includes the steps of: (a) disposing a first mask layer and a second mask layer respectively aside a front surface of a first substrate and aside a rear surface of the first substrate, wherein the first substrate is transparent to predetermined light; (b) forming a photoresist layer on the front surface of the first substrate and the first mask layer; (c) providing the predetermined light to illuminate the first substrate in a direction from the rear surface of the first substrate to the front surface of the first substrate so as to expose the photoresist layer to form an exposed portion and an unexposed portion; and (d) removing the unexposed portion to form the micro-needle structure by the exposed portion.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

FIGS. 1A to 1E are schematic illustrations showing a method of manufacturing a hollow micro-needle structure according to a first embodiment of the invention. As shown in FIGS. 1A to 1E, the method of manufacturing the hollow micro-needle structure according to the invention includes the following steps.

Figure 1A:
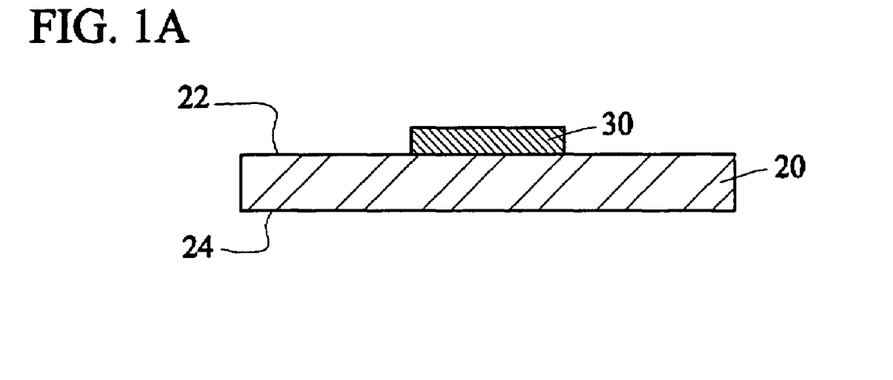
FIGS. 1A to 1E are schematic illustrations showing a method of manufacturing a hollow micro-needle structure according to a first embodiment of the invention.
Figure 1B:
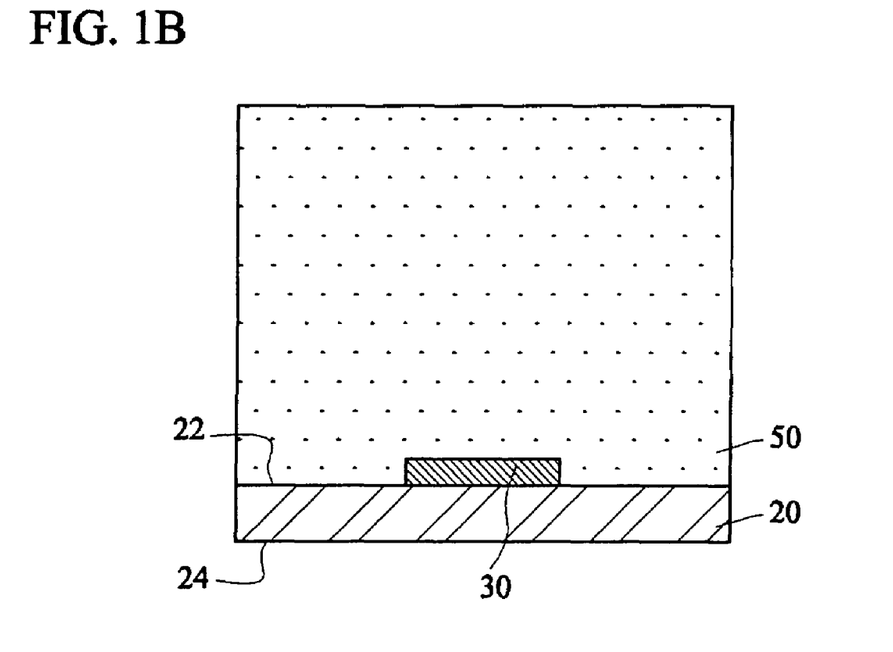
Figure 1C:
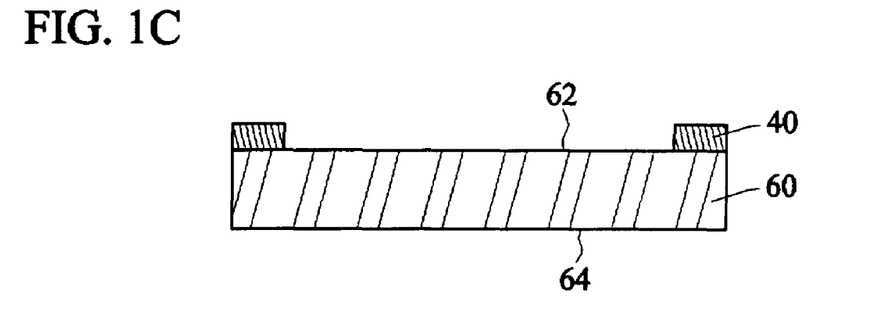
Figure 1D:
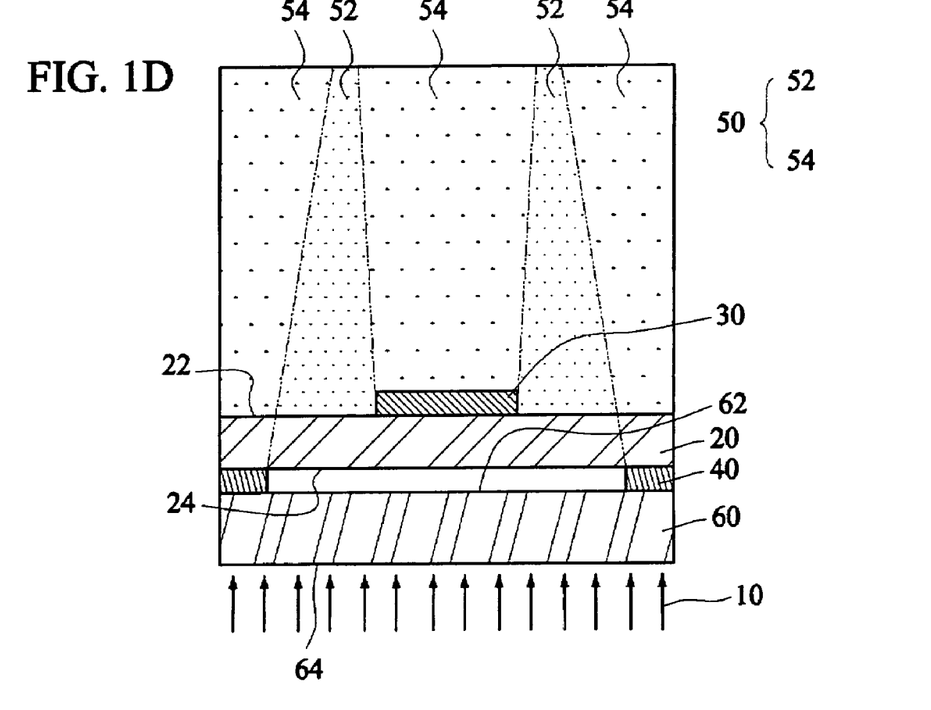
Figure 1E:
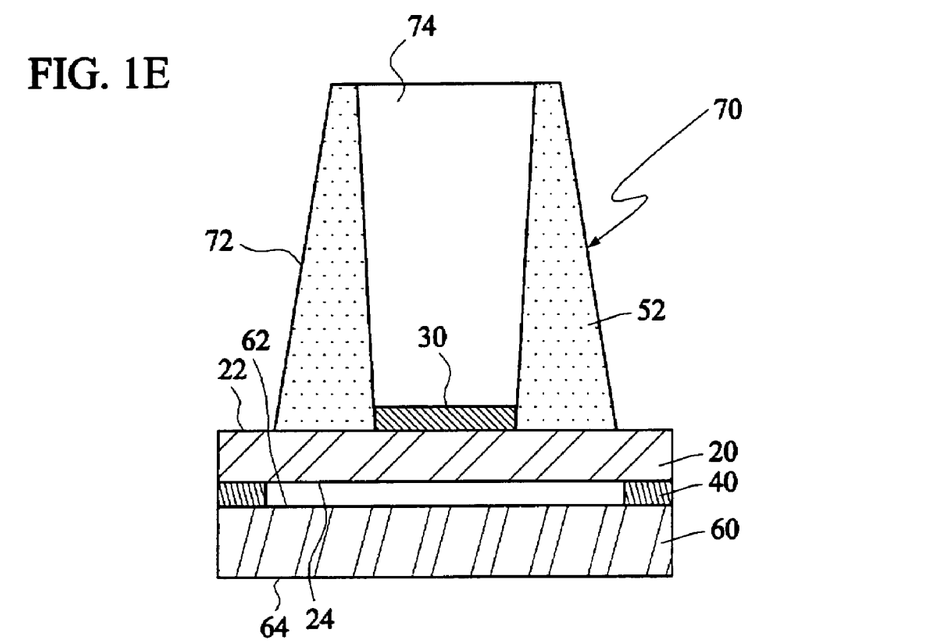

First, as shown in FIG. 1A, a first mask layer 30 is disposed or formed on a front surface 22 of a first substrate 20, wherein the first substrate 20 is transparent to predetermined light 10 (see FIG. 1D). The first mask layer 30 may have a circular shape, an elliptic shape, a rectangular shape or a polygonal shape.

Next, as shown in FIG. 1B, a photoresist layer 50 is formed on the front surface 22 of the first substrate 20 and the first mask layer 30. The photoresist layer 50 is a negative photoresist layer made of, for example, SU-8. It is to be noted that a conoid micro-needle structure may be formed using SU-8 in conjunction with an ultra-violet ray in one example of the invention.

On the other hand, as shown in FIG. 1C, a second mask layer 40 is formed on a front surface 62 of a second substrate 60, wherein the second substrate 60 is transparent to the predetermined light 10. The second mask layer 40 may have a circular shape, an elliptic shape, a rectangular shape or a polygonal shape. Alternatively, the second mask layer 40 may also be directly formed on a rear surface 24 of the first substrate 20, or the second mask layer 40 may be formed on a rear surface 64 of the second substrate 60. In this case, the front surface 62 of the second substrate 60 may be attached to the rear surface 24 of the first substrate 20 so that the second substrate 60 is interposed between the second mask layer 40 and the first substrate 20.

Next, after the first mask layer 30 and the second mask layer 40 are ready, as shown in FIG. 1D, the second mask layer 40 is disposed on the rear surface 24 of the first substrate 20 with the second mask layer 40 being attached to the rear surface 24 of the first substrate 20. The front surface 62 of the second substrate 60 and the rear surface 24 of the first substrate 20 are separated from each other by a gap and by the second mask layer 40. Alternatively, no gap exists between the second substrate 60 and the first substrate 20.

It is to be noted that the effect of the invention may be achieved as long as the first mask layer 30 and the ring-shaped second mask layer 40 may be respectively disposed aside the front surface 22 of the first substrate 20 and aside the rear surface 24 of the first substrate 20 with the first mask layer 30 being disposed in the ring-shaped second mask layer 40. It is to be noted that the ring-shape includes, without limitation to, a circular ring-shape and a polygonal ring-shape.

Each of the first substrate and the second substrate may be made of quartz, glass, a polymeric material, cyclic olefin copolymer (COC) or silicon. The predetermined light may be an ultra-violet ray, a laser beam, an excimer laser beam, an X ray or a synchrotron radiation X ray. The first or second mask layer may be made of a metal material, which includes chromium, chromium dioxide, gold, aluminum, titanium, copper, nickel, or a nickel cobalt alloy.

Then, as shown in FIG. 1D, the predetermined light 10 is provided to illuminate the first substrate 20 in a direction from the rear surface 24 to the front surface 22 so as to expose the photoresist layer 50 to form an exposed portion 52 and an unexposed portion 54, which are divided by several phantom lines of FIG. 1D. In this embodiment, the travelling direction of the predetermined light 10 is perpendicular to the rear surface 24 of the first substrate 20, or may be not perpendicular to the rear surface 24 of the first substrate 20 so that the exposed portion and the unexposed portion with different shapes may be formed.

Then, as shown in FIG. 1D, the unexposed portion 54 is removed by way of, for example, the development to form a micro-needle structure 70 by the exposed portion 52. The micro-needle structure 70 has an inclined sidewall 72 and a through hole 74 surrounded by the inclined sidewall 72, and the through hole 74 may serve as an air passage for the fluid.

Figure 2A:
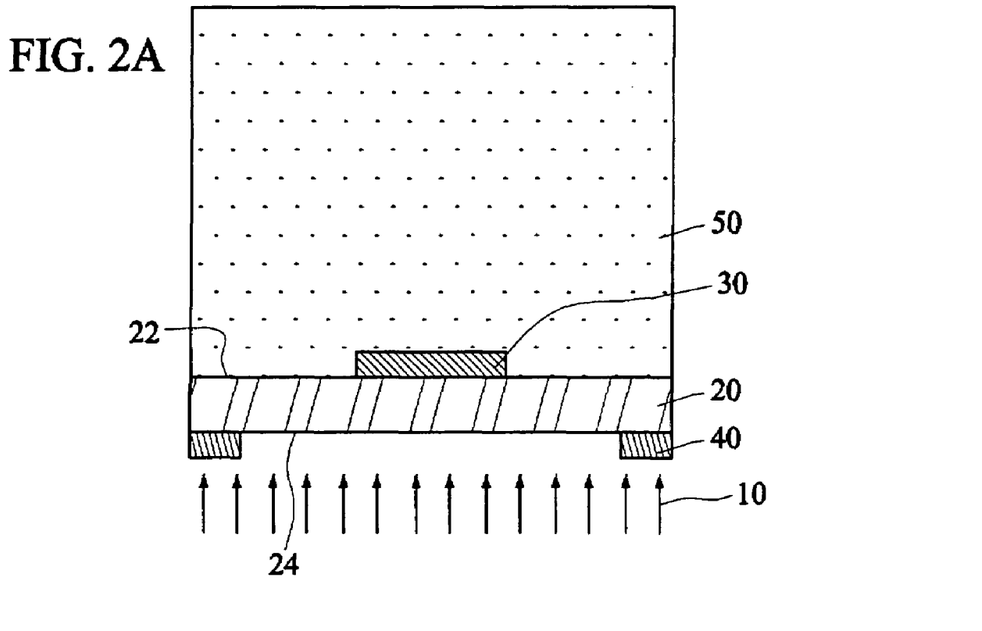
FIGS. 2A and 2B are partially schematic illustrations showing methods of manufacturing hollow micro-needle structures according to second and third embodiments of the invention.
Figure 2B:
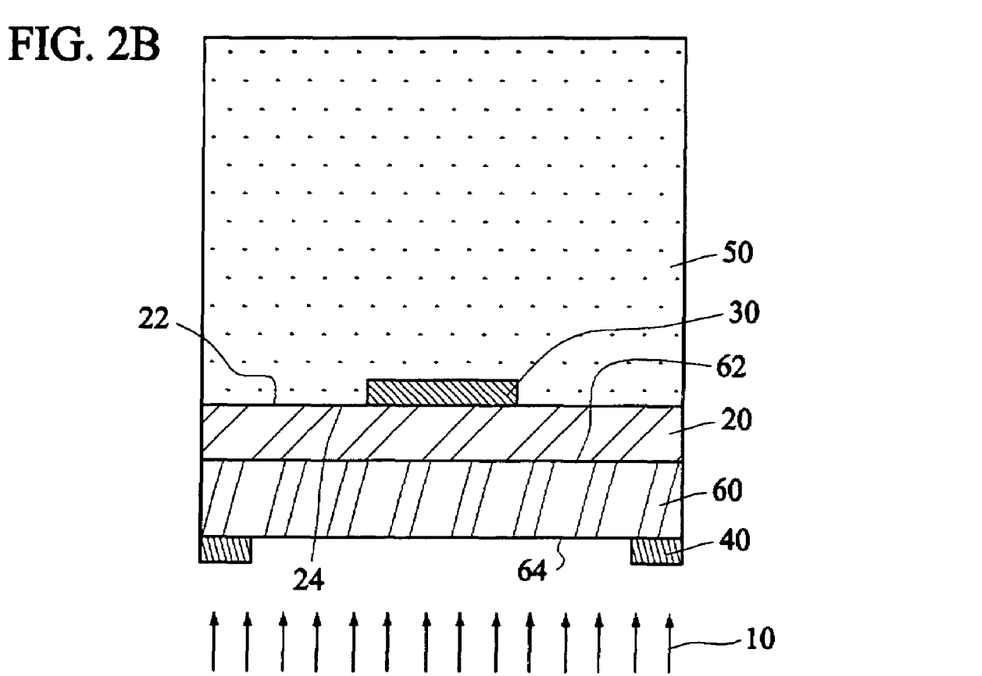

FIGS. 2A and 2B are partially schematic illustrations showing methods of manufacturing hollow micro-needle structures according to second and third embodiments of the invention. As shown in FIG. 2A, the first mask layer 30 and the second mask layer 40 according to the second embodiment are respectively formed on the front surface 22 and the rear surface 24 of the first substrate 20. As shown in FIG. 2B, the second mask layer 40 may be formed on the rear surface 64 of the second substrate 60 in the third embodiment. Then, the second mask layer 40 is disposed aside the rear surface 24 of the first substrate 20 with the front surface 62 of the second substrate 60 being attached to the rear surface 24 of the first substrate 20.

Figure 3A:
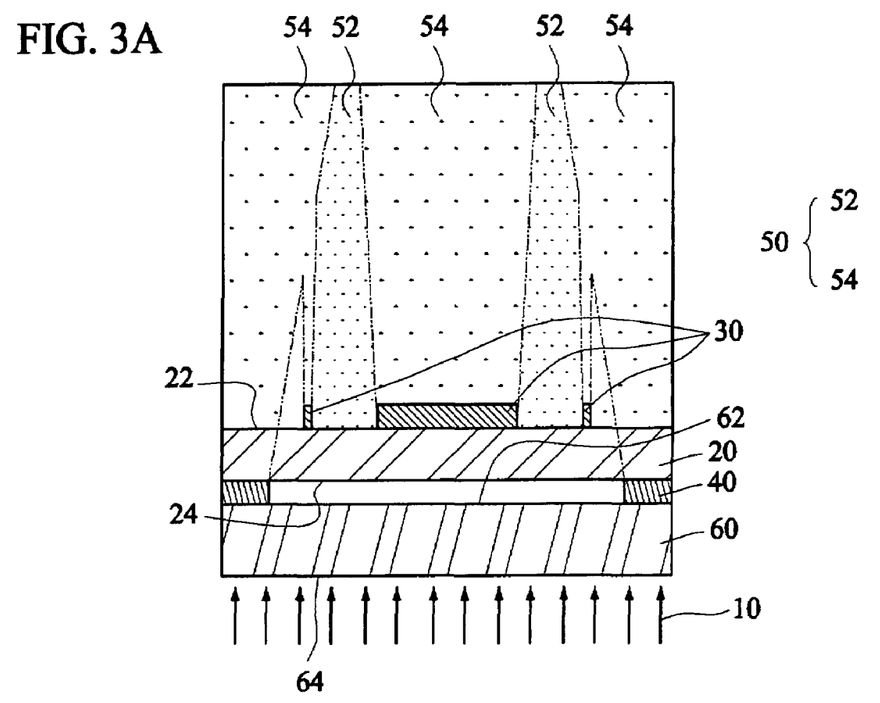
FIGS. 3A and 3B are partially schematic illustrations showing a method of manufacturing a hollow micro-needle structure according to a fourth embodiment of the invention.
Figure 3B:
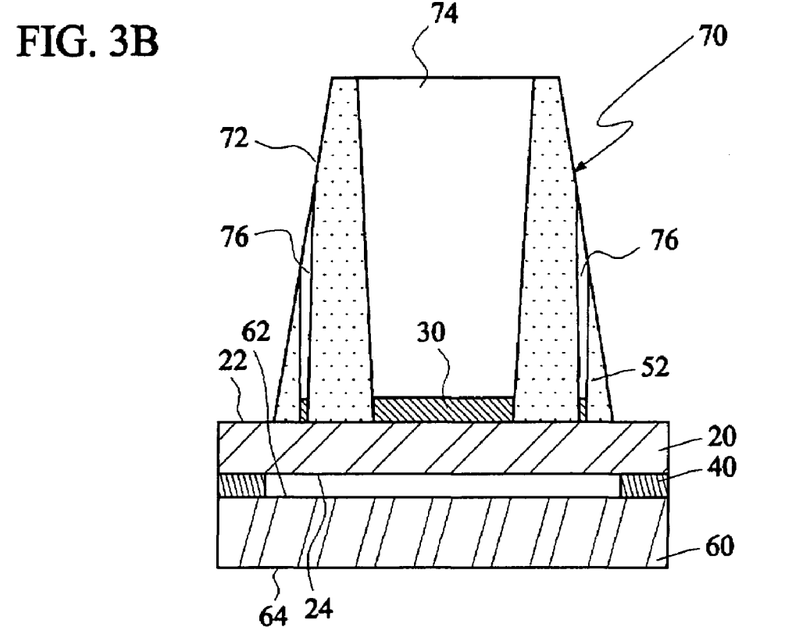

FIGS. 3A and 3B are partially schematic illustrations showing a method of manufacturing a hollow micro-needle structure according to a fourth embodiment of the invention. As shown in FIGS. 3A and 3B, the steps of the method of this embodiment are the same as those of the first embodiment except for the pattern of the first mask layer 30. Thus, the formed micro-needle structure 70 further has at least one sidewall hole 76 penetrating through the inclined sidewall 72.

Figure 4A:
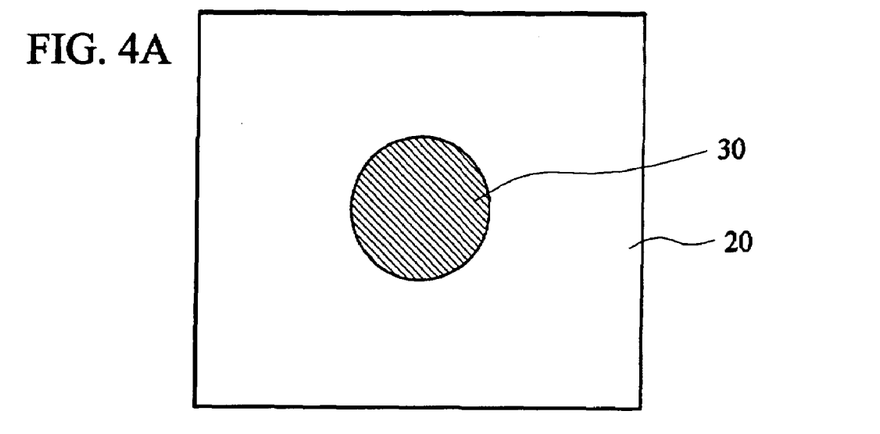
FIGS. 4A to 4C shows patterns of three kinds of first mask layers according to the invention.
Figure 4B:
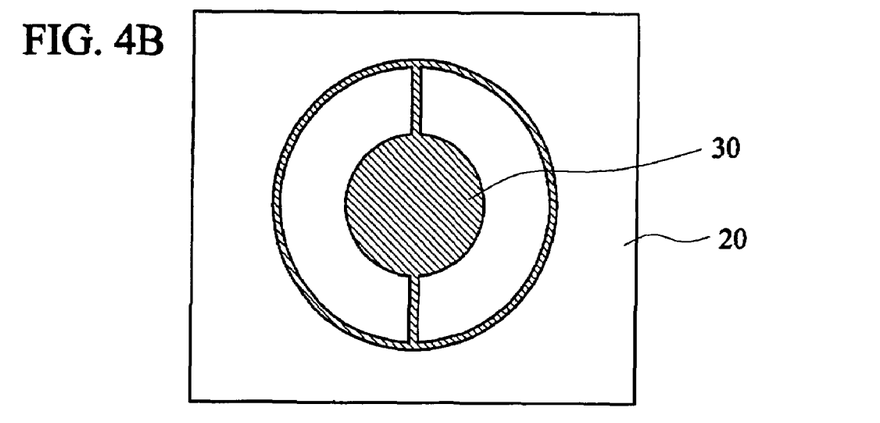
Figure 4C:
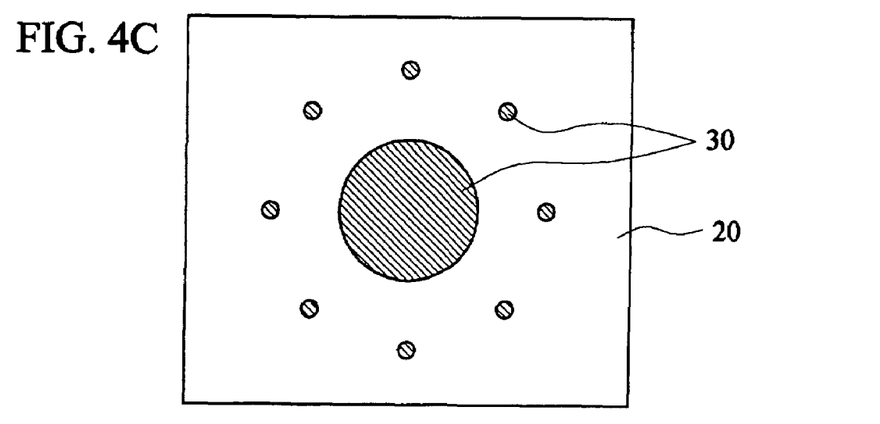
Figure 5A:
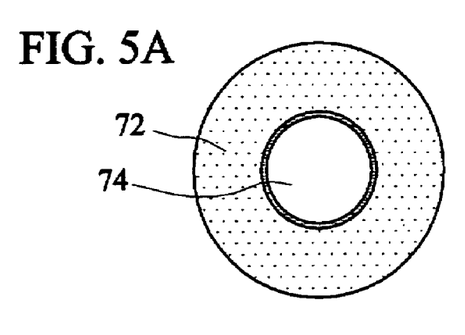
FIGS. 5A to 5C are respectively a top view, a front view and a pictorial view showing a hollow micro-needle structure, which is manufactured by each of the methods of the first to third embodiments in conjunction with the first mask layer of FIG. 4A.
Figure 5B:
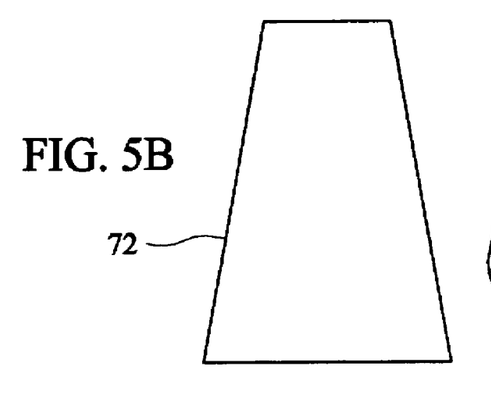
Figure 5C:
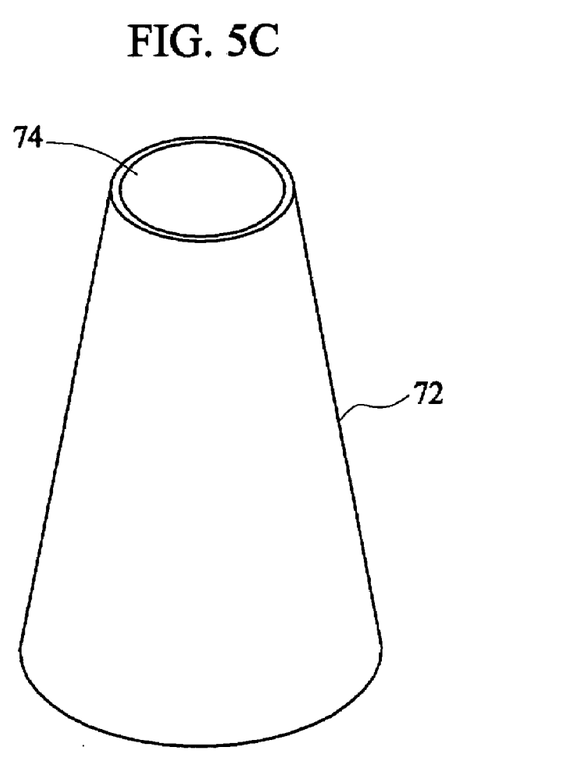
Figure 6A:
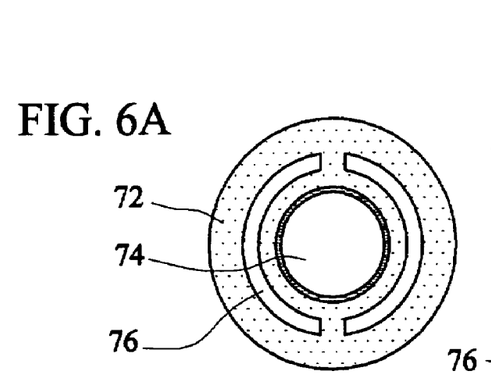
FIGS. 6A to 6C are respectively a top view, a front view and a pictorial view showing a hollow micro-needle structure, which is manufactured by the method of the fourth embodiment in conjunction with the first mask layer of FIG. 4B.
Figure 6B:
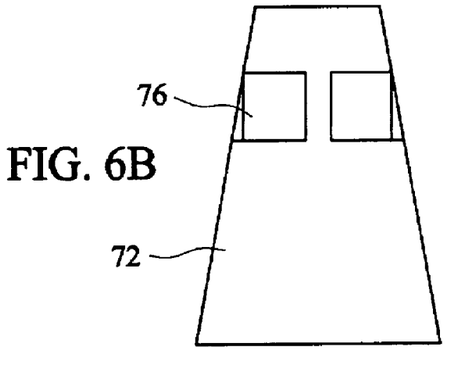
Figure 6C:
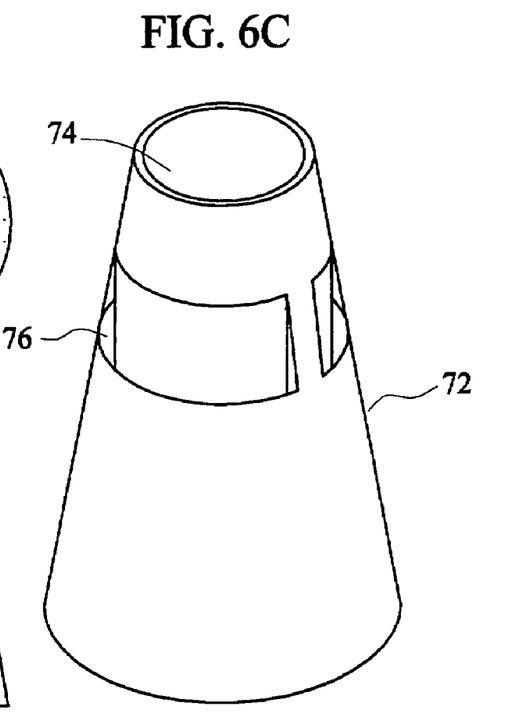
Figures 7A, 7B, 7C:
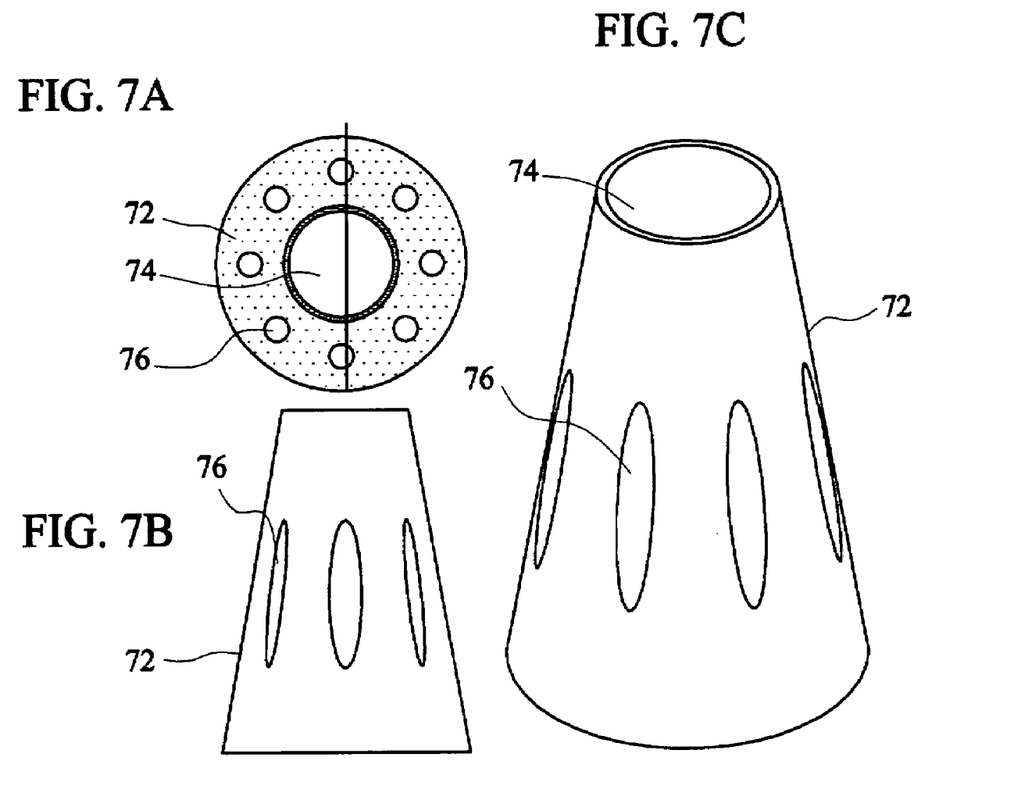
FIGS. 7A to 7C are respectively a top view, a front view and a pictorial view showing a hollow micro-needle structure, which is manufactured by the method of the fourth embodiment in conjunction with the first mask layer of FIG. 4C.

FIGS. 4A to 4C shows patterns of three kinds of first mask layers according to the invention. As shown in FIG. 4A, the pattern of the first mask layer 30 on the first substrate 20 corresponds to the methods of FIGS. 1A to 1E and FIGS. 2A and 2B, and the formed micro-needle structure is a conoid, as shown in FIGS. 5A to 5C. As shown in FIG. 4B, the pattern of the first mask layer 30 corresponds to the method of FIG. 3A and 3B, and the formed micro-needle structure is shown in FIGS. 6A to 6C. As shown in FIG. 4C, the pattern of the first mask layer 30 also corresponds to the method of FIGS. 3A and 3B, and the formed micro-needle structure is shown in FIGS. 7A to 7C.

Figure 8A:
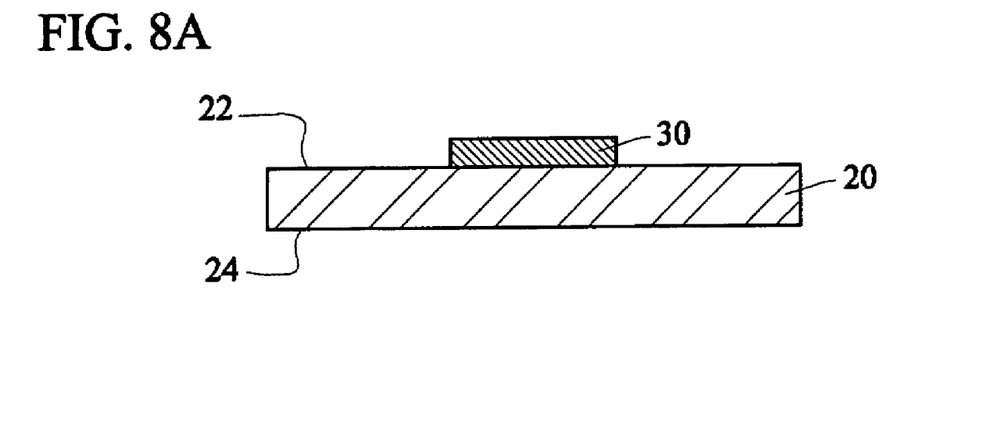
FIGS. 8A to 8D are schematic illustrations showing a method of manufacturing a hollow micro-needle structure according to a fifth embodiment of the invention.
Figure 8B:
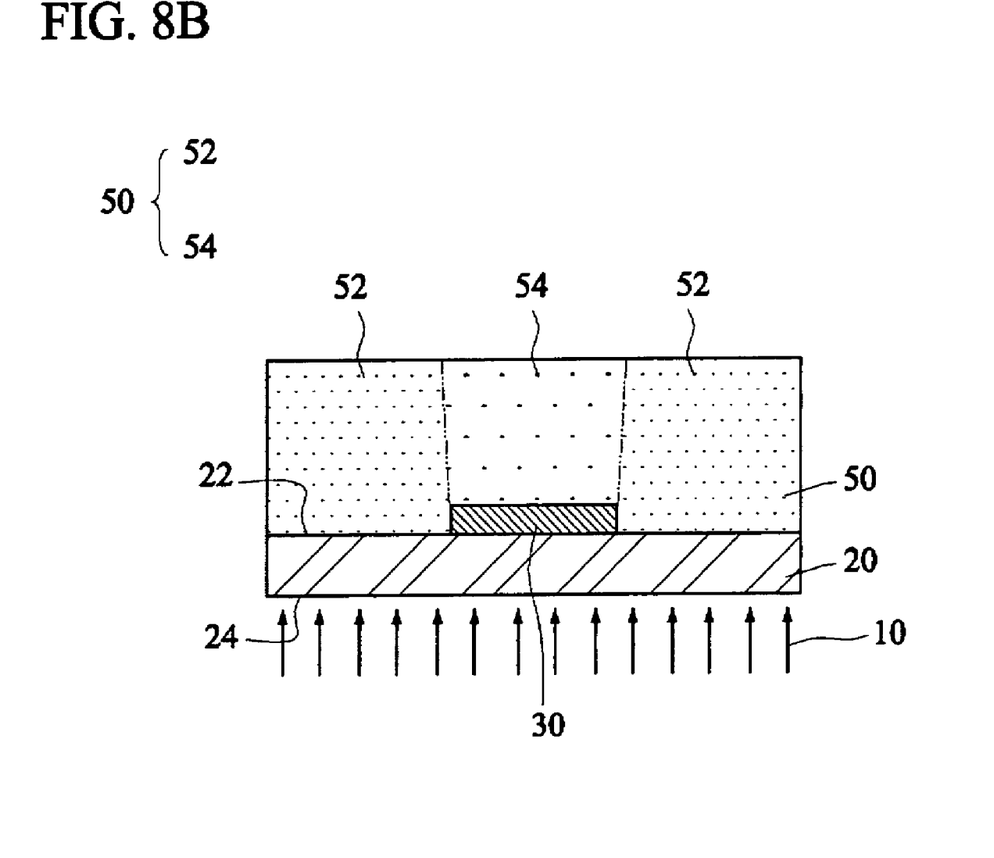
Figure 8C:
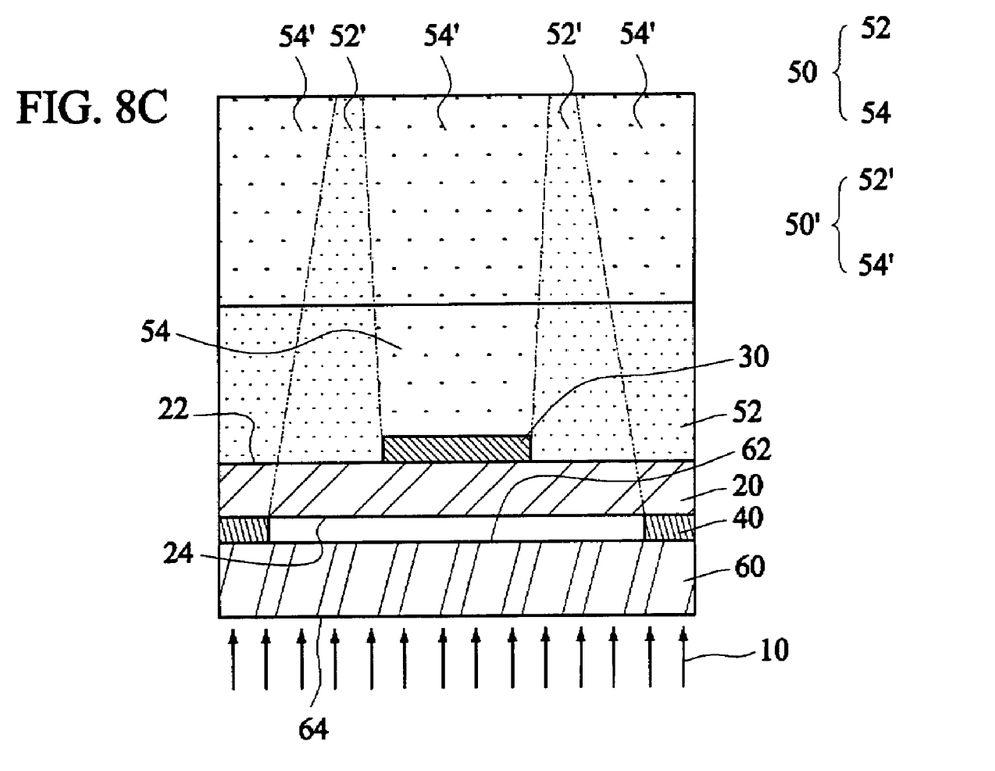
Figure 8D:
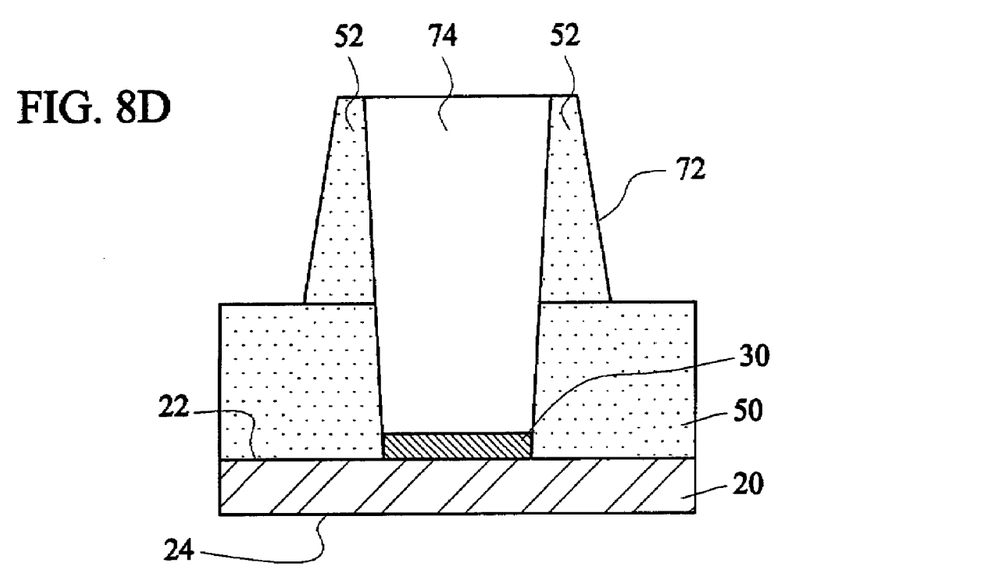

FIGS. 8A to 8D are schematic illustrations showing a method of manufacturing a hollow micro-needle structure according to a fifth embodiment of the invention. As shown in FIG. 8A, a first mask layer 30 is first disposed on a front surface 22 of a first substrate 20, wherein the first substrate 20 is transparent to predetermined light 10. Then, as shown in FIG. 8B, a first photoresist layer 50 is formed on the front surface 22 of the first substrate 20 and the first mask layer 30. Next, the predetermined light 10 is provided to illuminate the first substrate 20 in a direction from a rear surface 24 to the front surface 22 so as to expose the first photoresist layer 50 to form a first exposed portion 52 and a first unexposed portion 54. Then, as shown in FIG. 8C, a second photoresist layer 50' is formed on the first photoresist layer 50, and then a second mask layer 40 is disposed on a front surface 62 of a second substrate 60, wherein the second substrate 60 is transparent to the predetermined light 10. Alternatively, the second mask layer 40 may also be disposed on a rear surface 64 of the second substrate 60. Next, the second substrate 60 is placed on the rear surface 24 of the first substrate 20. Then, the predetermined light 10 is provided to illuminate the second substrate 60 in a direction from the rear surface 64 to the front surface 22 of the first substrate 20 so as to expose the second photoresist layer 50' to form a second exposed portion 52' and a second unexposed portion 54'. Next, as shown in FIG. 8D, the first unexposed portion 54 and the second unexposed portion 54' are removed. Then, the first photoresist layer 50 and the first substrate 20 are separated from each other to form the micro-needle structure. In this case, the micro-needle structure is composed of the first exposed portion 52 of the first photoresist layer 50 and the second exposed portion 52' of the second photoresist layer 50', and has an inclined sidewall 72 and a through hole 74 surrounded by the inclined sidewall 72.

Thus, the micro-needle structure of this embodiment has the first photoresist layer 50 serving as a base. One of ordinary skill in the art may easily understand that multiple first mask layers 30 and multiple second mask layers 40 may be arranged to form multiple micro-needle structures on the first photoresist layer 50. The micro-needle structures may be arranged in an array on the base and may be applied to the opto-electronic industry, the medical industry and the cosmetic industry.

Similarly, the structure of FIGS. 3A and 3B may also be formed on the base. Because one of ordinary skill in the art may easily understand that the pattern of the mask layer may be properly modified, detailed descriptions thereof will be omitted. In addition, all the applications and features of the above-mentioned embodiments may also be applied to the fifth embodiment.

Thus, only one exposure-development procedure is needed to finish the hollow micro-needle structure according to the method of manufacturing the hollow micro-needle structure of the invention. Adjusting the patterns of the first mask layer and the second mask layer can adjust the structure of the micro-needle structure. In addition, the micro-needle structure may be formed into the conoid due to the property of generating the conoid exposed portion when the SU-8 is exposed to the ultra-violet ray. Also, the holes serving as air passages may be formed on the top surface and the inclined sidewall of the micro-needle structure. The sidewall hole 76 may also split the fluid of the through hole 74. Furthermore, the hollow micro-needle array structure, which may be applied to the biometric fluid sampling process or the opto-electronic industry (e.g., serving as electrodes), may be formed on the first substrate according to the design of the patterns of the first mask layer and the second mask layer although the descriptions mentioned hereinabove are made with respect to the single micro-needle structure.

While the invention has been described by way of examples and in terms of preferred embodiments, it is to be understood that the invention is not limited thereto. To the contrary, it is intended to cover various modifications. Therefore, the scope of the appended claims should be accorded the broadest interpretation so as to encompass all such modifications.

What is claimed is:

1. A method of manufacturing a hollow micro-needle structure, the method comprising the steps of:
    (a) disposing a first mask layer and a second mask layer respectively aside a front surface of a first substrate and aside a rear surface of the first substrate, wherein the first substrate is transparent to predetermined light;
    (b) forming a photoresist layer on the front surface of the first substrate and the first mask layer;
    (c) providing the predetermined light to illuminate the first substrate in a direction from the rear surface of the first substrate to the front surface of the first substrate so as to expose the photoresist layer to form an exposed portion and an unexposed portion; and
    (d) removing the unexposed portion to form the micro-needle structure by the exposed portion.

2. The method according to claim 1, wherein the photoresist layer is a negative photoresist layer.

3. The method according to claim 1, wherein each of the first and second mask layers is made of a metal material.

4. The method according to claim 1, wherein the first mask layer has a circular shape, an elliptic shape, a rectangular shape or a polygonal shape.

5. The method according to claim 1, wherein the second mask layer has a circular shape, an elliptic shape, a rectangular shape or a polygonal shape.

6. The method according to claim 1, wherein the second mask layer is directly formed on the rear surface of the first substrate.

7. The method according to claim 1, wherein the step (a) comprises the sub-steps of:
    (a1) forming the second mask layer on a front surface of a second substrate, wherein the second substrate is transparent to the predetermined light; and
    (a2) disposing the second mask layer on the rear surface of the first substrate with the second mask layer being attached to the rear surface of the first substrate.

8. The method according to claim 1, wherein the step (a) comprises the sub-steps of:
    (a1) forming the second mask layer on a rear surface of a second substrate, wherein the second substrate is transparent to the predetermined light; and
    (a2) attaching a front surface of the second substrate to the rear surface of the first substrate so that the second substrate is interposed between the second mask layer and the first substrate.

9. The method according to claim 1, wherein the micro-needle structure is a hollow conoid, a hollow tetrahedron or a hollow polyhedron.

10. The method according to claim 1, wherein the second mask layer is a ring, and the first mask layer is disposed inside the second mask layer of the ring so that the micro-needle structure has an inclined sidewall and a through hole surrounded by the inclined sidewall.

11. The method according to claim 10, wherein the micro-needle structure further has at least one sidewall hole penetrating through the inclined sidewall.

12. A method of manufacturing a hollow micro-needle structure, the method comprising the steps of:
    (a) disposing a first mask layer on a front surface of a first substrate, wherein the first substrate is transparent to predetermined light;
    (b) forming a first photoresist layer on the front surface of the first substrate and the first mask layer;
    (c) providing the predetermined light to illuminate the first substrate in a direction from a rear surface of the first substrate to the front surface of the first substrate so as to expose the first photoresist layer to form a first exposed portion and a first unexposed portion;
    (d) forming a second photoresist layer on the first photoresist layer;
    (f) disposing a second mask layer on a surface of a second substrate, wherein the second substrate is transparent to the predetermined light;
    (g) disposing the second substrate on the rear surface of the first substrate;
    (h) providing the predetermined light to illuminate the second substrate in a direction from the second substrate to the first substrate so as to expose the second photoresist layer to form a second exposed portion and a second unexposed portion;

(i) removing the first unexposed portion and the second unexposed portion; and (j) separating the first photoresist layer from the first substrate to form the micro-needle structure, which is composed of the first exposed portion of the first photoresist layer and the second exposed portion of the second photoresist layer, and has an inclined sidewall and a through hole surrounded by the inclined sidewall.

13. The method according to claim 12, wherein each of the first and second mask layers is made of a metal material.

14. The method according to claim 12, wherein the second mask layer is formed on a front surface or a rear surface of the second substrate.

15. The method according to claim 12, wherein the micro-needle structure is a hollow conoid, a hollow tetrahedron or a hollow polyhedron.

16. The method according to claim 15, wherein the micro-needle structure further has at least one sidewall hole penetrating through the inclined sidewall.

* * * * *